United States Patent
Honda et al.

(10) Patent No.: US 10,441,309 B2
(45) Date of Patent: Oct. 15, 2019

(54) ENERGY TREATMENT INSTRUMENT

(71) Applicant: OLYMPUS CORPORATION, Hachioji-shi, Tokyo (JP)

(72) Inventors: Yoshitaka Honda, Hachioji (JP); Tatsuro Yamamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/596,234

(22) Filed: May 16, 2017

(65) Prior Publication Data

US 2017/0245880 A1 Aug. 31, 2017

Related U.S. Application Data

(63) Continuation of application No. PCT/JP2016/061721, filed on Apr. 11, 2016.

(30) Foreign Application Priority Data

Apr. 21, 2015 (JP) ................. 2015-086779

(51) Int. Cl.
*A61B 17/32* (2006.01)
*A61B 18/12* (2006.01)
(Continued)

(52) U.S. Cl.
CPC ........... *A61B 17/320068* (2013.01); *A61B 17/320092* (2013.01); *A61B 18/1206* (2013.01);
(Continued)

(58) Field of Classification Search
None
See application file for complete search history.

(56) References Cited

U.S. PATENT DOCUMENTS 6,666,875 B1 12/2003 Sakurai et al.
2003/0192557 A1* 10/2003 Krag ............... A61B 17/32053
128/898

(Continued)

FOREIGN PATENT DOCUMENTS

CN 104283333 A 1/2015
JP 2000-254141 A 9/2000
(Continued)

OTHER PUBLICATIONS

Kesler, Morris, "Highly Resonant Wireless Power Transfer: Safe, Efficient, and over Distance", WiTricity, 2013, <https://pdfs.semanticscholar.org/c936/2f360a77b62cdb79d101c8fb4fc2661a905f.pdf>.*

(Continued)

*Primary Examiner* — Linda C Dvorak
*Assistant Examiner* — Ryan T Clark
(74) *Attorney, Agent, or Firm* — Oliff PLC

(57) ABSTRACT

An energy treatment instrument includes a held unit capable of being held, and an electric-receiver-side resonator including an electric receiver coil wound around a coil axis, and resonating at the same resonance frequency as an electric-supplier-side resonator, thereby electric power being supplied from an electric supplier coil to the electric receiver coil. The energy treatment instrument includes an energy generator generating energy for use in a treatment by using the electric power supplied to the electric receiver coil, and a magnetic member including a magnetic material and located distant from the coil axis of the electric receiver coil.

17 Claims, 10 Drawing Sheets

(51) Int. Cl.
    *A61B 18/14*     (2006.01)
    *A61B 17/00*     (2006.01)
    *A61B 18/00*     (2006.01)

(52) U.S. Cl.
    CPC ...... *A61B 18/1445* (2013.01); *A61B 18/1482* (2013.01); *A61B 2017/00411* (2013.01); *A61B 2018/00994* (2013.01); *A61B 2018/126* (2013.01); *A61B 2018/1226* (2013.01); *A61B 2018/1286* (2013.01); *A61B 2018/145* (2013.01)

(56) References Cited

U.S. PATENT DOCUMENTS

| | | | | |
|---|---|---|---|---|
| 2004/0116952 | A1* | 6/2004 | Sakurai | A61B 17/1628 606/169 |
| 2009/0090763 | A1* | 4/2009 | Zemlok | A61B 17/07207 227/175.2 |
| 2011/0115891 | A1* | 5/2011 | Trusty | A61B 1/00016 348/65 |
| 2014/0005681 | A1* | 1/2014 | Gee | A61B 17/320092 606/130 |
| 2014/0333148 | A1 | 11/2014 | Uchida | |
| 2015/0209035 | A1* | 7/2015 | Zemlok | G01D 18/008 73/1.01 |
| 2016/0111886 | A1* | 4/2016 | Sherman | H02J 7/025 307/104 |

FOREIGN PATENT DOCUMENTS

| | | |
|---|---|---|
| JP | 2000-358301 A | 12/2000 |
| JP | 2014-68987 A | 4/2014 |
| JP | 2015-53980 A | 3/2015 |
| JP | 2015-66079 A | 4/2015 |
| WO | 2013/111344 A1 | 8/2013 |
| WO | 2014/112155 A1 | 7/2014 |

OTHER PUBLICATIONS

Jul. 12, 2016 International Search Report issued with International Patent Application No. PCT/JP2016/061721.
Nov. 2, 2017 International Preliminary Report on Patentability issued in International Application No. PCT/JP2016/061721.
Nov. 19, 2018 Extended European Search Report Issued in European Patent Application No. 16783046.2.
Nov. 28, 2018 Office Action Issued in Chinese Patent Application No. 201680004173.8.
Jul. 22, 2019 Office Action issued in Chinese Patent Application No. 201680004173.8.

\* cited by examiner

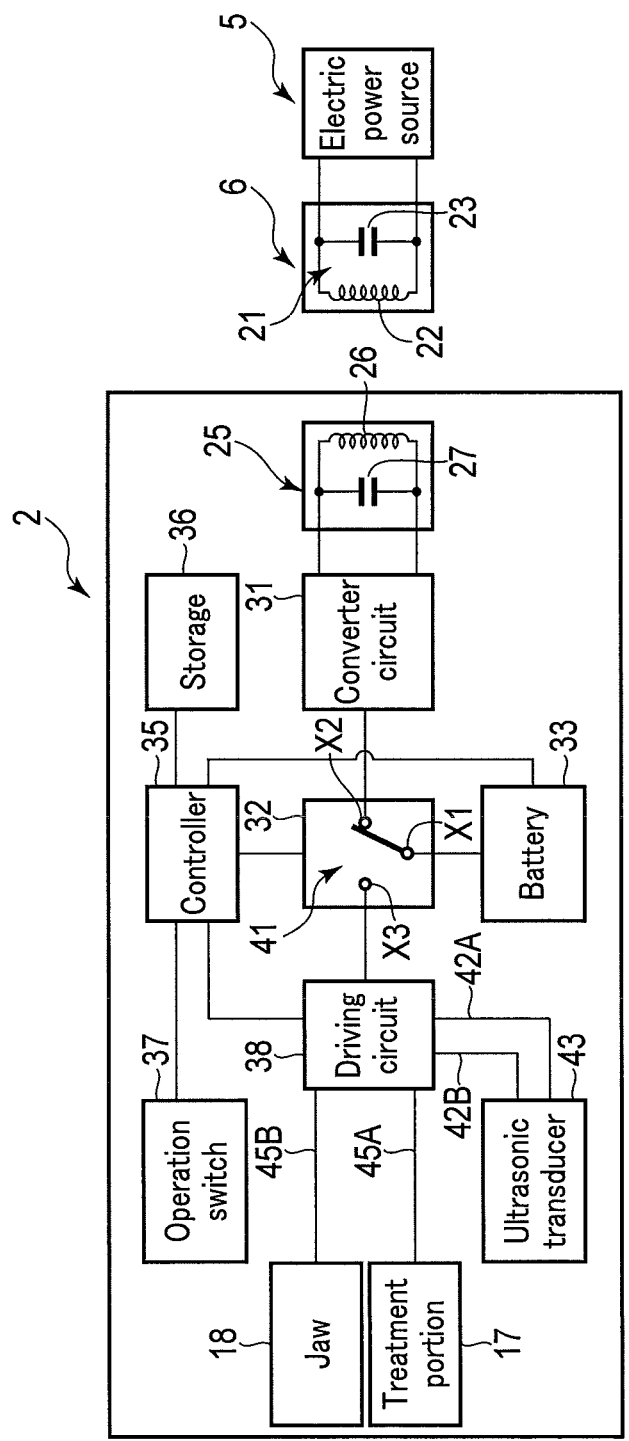
F I G. 2

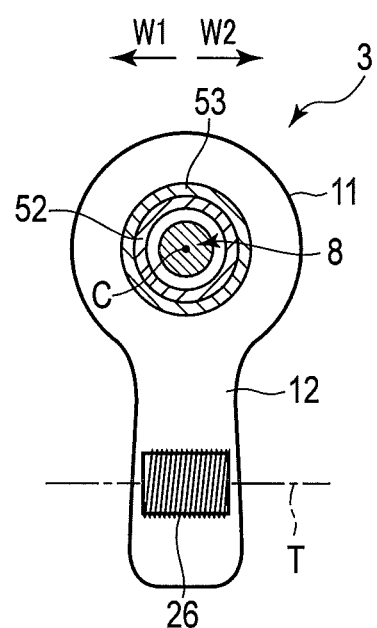
F I G. 4

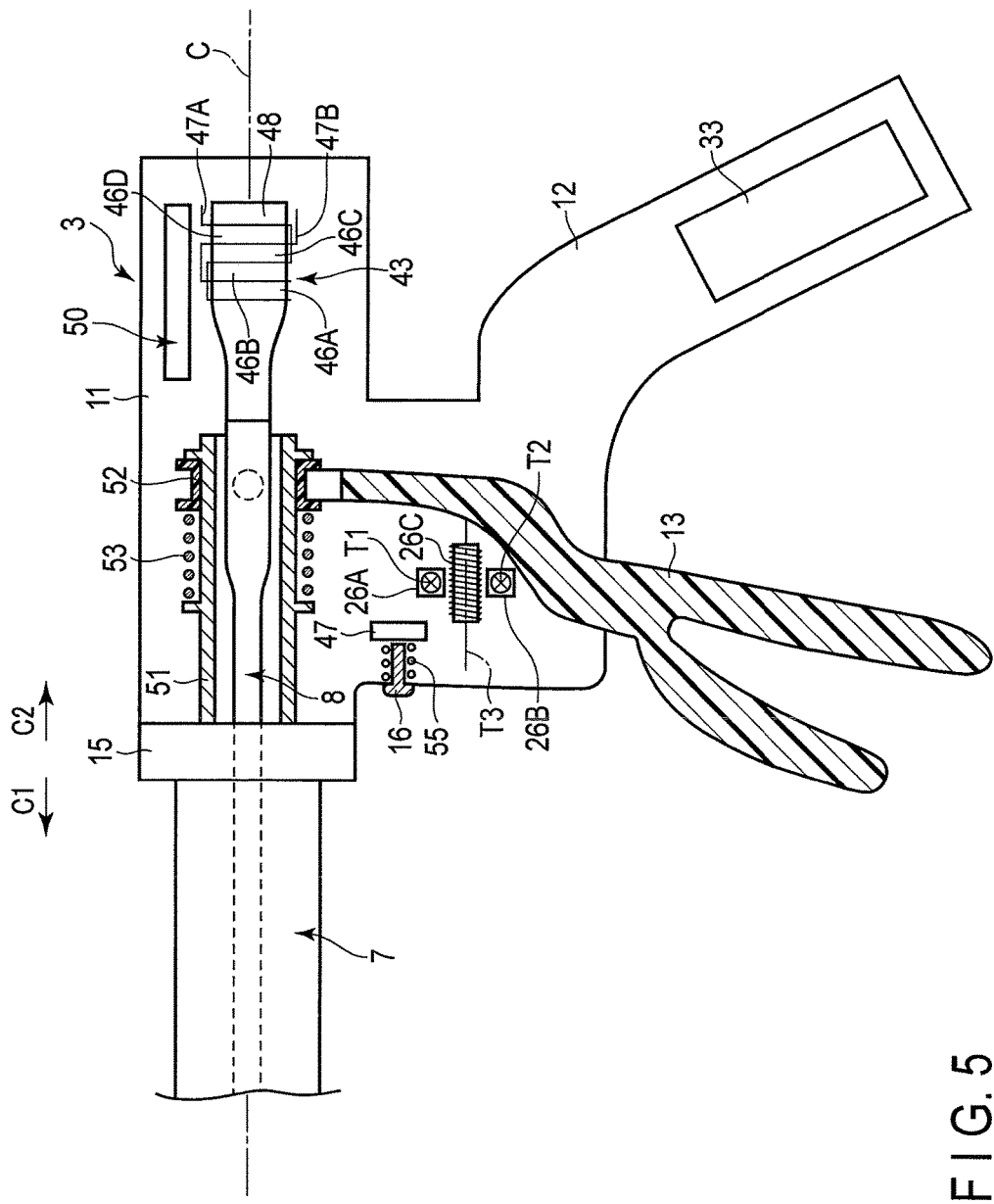
F I G. 5

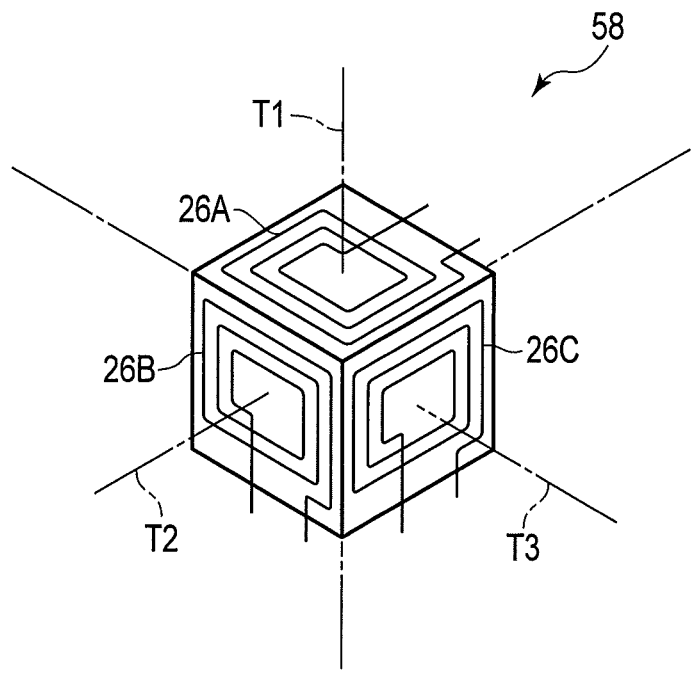
F I G. 8
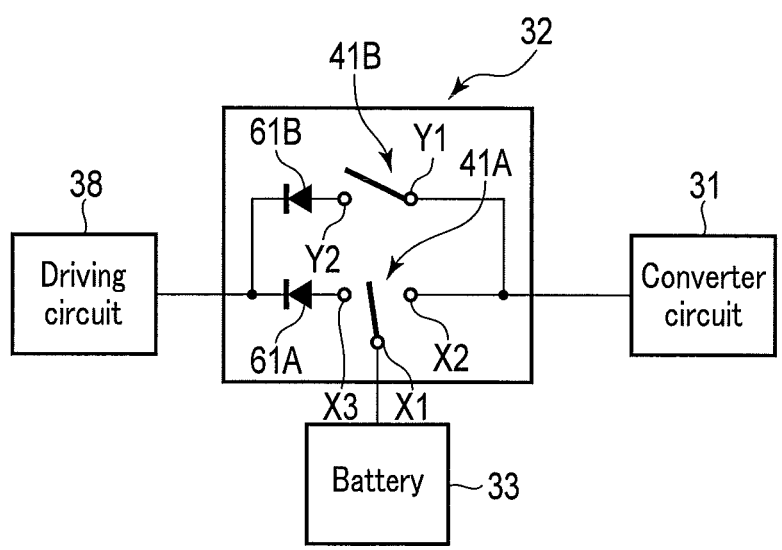
F I G. 9

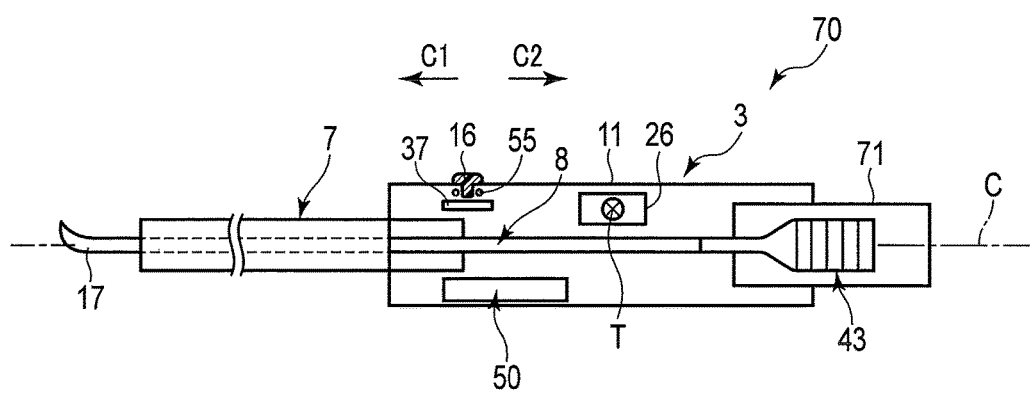
F I G. 12

ENERGY TREATMENT INSTRUMENT

CROSS-REFERENCE TO RELATED APPLICATIONS

This is a Continuation application of PCT Application No. PCT/JP2016/061721, filed Apr. 11, 2016 and based upon and claiming the benefit of priority from prior Japanese Patent Application No. 2015-086779, filed Apr. 21, 2015, the entire contents of which are incorporated herein by reference.

BACKGROUND OF THE INVENTION

1. Field of the Invention

The present invention relates to an energy treatment instrument which generates energy by being supplied with electric power, and performs a treatment by using the generated energy.

2. Description of the Related Art

Jpn. Pat. Appln. KOKAI Publication No. 2014-68987 discloses an energy treatment instrument which performs a treatment by using high-frequency energy (high-frequency electric power) as energy. In this energy treatment instrument, high-frequency electric power is supplied to a pair of treatment electrodes, and a treated target, which is grasped between the treatment electrodes, is subjected to a bipolar treatment. In addition, in the energy treatment instrument, an electric receiver coil extends helically about a longitudinal axis between an inner cylinder portion and an outer cylinder portion, and an electric-receiver-side resonator is formed by the electric receiver coil and a capacitor. Besides, a trocar, through which the energy treatment instrument is inserted, is provided with an electric-supplier-side resonator which includes an electric supplier coil. By the electric-supplier-side resonator being supplied with electric power, and the electric-supplier-side resonator electrically resonating, the electric-receiver-side resonator electrically resonates at the same resonance frequency as the electric-supplier-side resonator. Thereby, in the state in which the electric-supplier-side resonator and the electric-receiver-side resonator are not electrically connected (i.e. by wireless transmission), electric power is supplied from the electric supplier coil to the electric receiver coil. The electric power, which is supplied to the electric receiver coil, is converted to high-frequency electric power by a converter circuit, and the high-frequency electric power is supplied to the treatment electrodes.

BRIEF SUMMARY OF THE INVENTION

According to one aspect of the invention, an energy treatment instrument including: a held unit which has a longitudinal axis, and which is capable of being held; a magnetic member including a magnetic material; an electric-receiver-side resonator including an electric receiver coil which is wound around a coil axis that is located distant from the magnetic member, the electric-receiver-side resonator being configured to resonate at the resonance frequency as an electric-supplier-side resonator including an electric supplier coil, thereby electric power being supplied from the electric supplier coil to the electric receiver coil; and an energy generator configured to generate energy for use in a treatment, by using the electric power supplied to the electric receiver coil.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic view illustrating a configuration which generates energy for use in a treatment in the energy treatment system according to the first embodiment, FIG. 4 is a schematic view illustrating the internal configuration of the held unit according to the first embodiment, by a cross section perpendicular to a longitudinal axis which passes through an electric receiver coil, FIG. 5 is a schematic view illustrating an internal configuration of a held unit according to a first modification, by a cross section perpendicular to the width direction of the held unit, FIG. 8 is a perspective view which schematically illustrates a loop antenna which is formed by an electric receiver coil according to a second modification, FIG. 9 is a schematic view illustrating a configuration of a relay circuit according to a third modification, FIG. 12 is a schematic view illustrating an energy treatment instrument according to a sixth modification.

DETAILED DESCRIPTION OF THE INVENTION

First Embodiment

Figure 1:
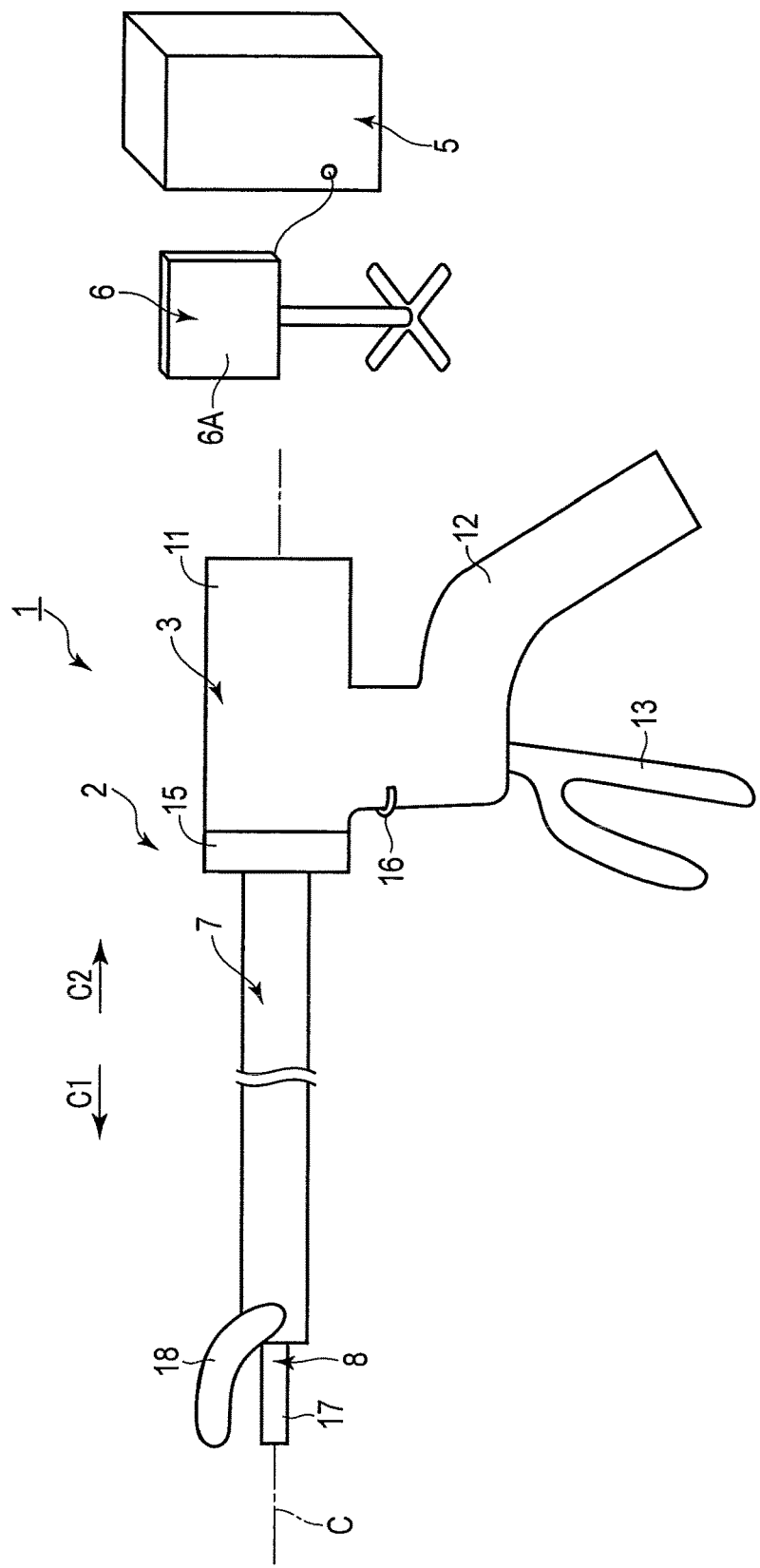
FIG. 1 is a schematic view illustrating an energy treatment system according to a first embodiment.

A first embodiment of the present invention will be described with reference to FIG. 1 to FIG. 4. FIG. 1 is a view illustrating an energy treatment system 1. As illustrated in FIG. 1, the energy treatment system 1 includes an energy treatment instrument (handpiece) 2. The energy treatment instrument 2 is a cordless treatment instrument which does not include a cable cord. The energy treatment instrument 2 includes a held unit (housing) 3 which can be held by a surgeon. The held unit 3 has a longitudinal axis C. Here, in the energy treatment instrument 2, one side of a direction along the longitudinal axis C is a distal side (an arrow C1 side in FIG. 1), and a side opposite to the distal side is a proximal side (an arrow C2 side in FIG. 1). In addition, the energy treatment system 1 includes an electric power source 5, and an electric supplier unit (electric supplier device) 6 which is electrically connected to the electric power source 5. The electric supplier unit 6 includes a magnetic force emission surface 6A which can emit a magnetic force. In the present embodiment, the electric power source 5 and electric supplier unit 6 are provided as a peripheral device of the energy treatment instrument 2, and is disposed on, for example, a trolley.

The held unit 3 of the energy treatment instrument 2 includes a case main body 11 which extends along the longitudinal axis C, with the axial center thereof substantially agreeing with the longitudinal axis C; a stationary handle (grip) 12 which extends from the case main body 11 in a direction crossing the longitudinal axis C; and a movable handle (handle) 13 which is openable and closable relative to the stationary handle 12. In addition, the held unit 3 includes a rotary operation knob (rotary operation portion) 15 which is coupled to the distal side of the case main body 11. The rotary operation knob 15 is rotatable relative to the case main body 11 around the longitudinal axis C. In the held unit 3, an energy operation input button (energy operation input portion) 16 is attached to that surface of the stationary handle 12, which faces the distal side. In the meantime, the case main body 11, stationary handle 12, movable handle 13, rotary operation knob 15 and energy operation input button 16 are formed of a non-magnetic material such as a resin. In addition, the opening and closing directions of the movable handle 13 are substantially parallel to the longitudinal axis C.

The energy treatment instrument 2 includes a sheath 7 which extends along the longitudinal axis C, with the axial center thereof substantially agreeing with the longitudinal axis C. The sheath 7 is coupled to the distal side of the held unit 3, in the state in which the sheath 7 is inserted, from the distal side, into the inside of the rotary operation knob 15 and the inside of the case main body 11. The sheath 7 is a magnetic member including a magnetic material such as stainless steel. In addition, in the energy treatment instrument 2, a vibration transmitter 8 extends from the inside of the case main body 11 toward the distal side through the inside of the sheath 7. The vibration transmitter 8 extends along the longitudinal axis C, with the axial center thereof substantially agreeing with the longitudinal axis C. The vibration transmitter 8 is formed of a material with high vibration transmissivity, such as Ti-6Al-4V or duralumin, and is formed of a non-magnetic material. In addition, a treatment portion 17 is provided in a distal portion of the vibration transmitter 8, and the treatment portion 17 projects toward the distal side from a distal end of the sheath 7.

In the energy treatment instrument 2, a jaw 18 is rotatably attached to a distal portion of the sheath 7. By opening or closing the movable handle 13 relative to the stationary handle 12, the jaw 18 opens or closes relative to the treatment portion 17 of the vibration transmitter 8. The jaw 18 is a magnetic member including a magnetic material. Here, the magnetic material includes iron, nickel, cobalt, cadmium, and alloys thereof. The non-magnetic material includes copper, aluminum, and a resin. By the rotary operation knob 15 rotating around the longitudinal axis C, the sheath 7, vibration transmitter 8 and jaw 18 rotate, together with the rotary operation knob 15, about the longitudinal axis C relative to the case main body 11. In addition, in a treatment, the distal portion of the sheath 7, treatment portion 17 and jaw 18 are inserted into a body cavity, such as a peritoneal cavity, through a hole of a trocar which is fixed to a body wall of the human body. Then, by closing the jaw 18 relative to the treatment portion 17, a treated target is grasped between the treatment portion 17 and jaw 18.

FIG. 2 is a view illustrating a configuration which generates energy for use in a treatment in the energy treatment system 1. Incidentally, the energy for use in the treatment includes high-frequency current, ultrasonic vibration, etc. which are directly applied to the treated target in the treatment, and also includes energy (e.g. vibration generating electric power for generating ultrasonic vibration) for generating energy that is applied to the treated target. As illustrated in FIG. 2, the electric supplier unit 6 includes an electric-supplier-side resonator 21. In the present embodiment, the electric-supplier-side resonator 21 is a resonance circuit in which an electric supplier coil 22 and an electric-supplier-side capacitor 23 are electrically connected in parallel relative to each other. In one example, the electric power source 5 supplies DC electric power from a battery (not shown), which is provided in the electric power source 5, to the electric-supplier-side resonator 21. In another example, electric power from a plug socket is converted to DC electric power by a converter circuit (not shown) which is provided in the electric power source 5, and the DC electric power is supplied to the electric-supplier-side resonator 21. In the electric-supplier-side resonator 21, the inductance of the electric supplier coil 22 and the capacitance of the electric-supplier-side capacitor 23 are set in such a state that the electric-supplier-side resonator 21 electrically resonates at a resonance frequency f0. Thus, by DC electric power being supplied to the electric-supplier-side resonator 21, the electric-supplier-side resonator (electric-supplier-side resonance circuit) 21 electrically resonates (naturally vibrates) at the resonance frequency (natural frequency) f0. Thereby, the DC electric power, which is supplied to the electric-supplier-side resonator 21, is converted to AC electric power (AC current) of the resonance frequency f0.

The energy treatment instrument 2 includes an electric-receiver-side resonator 25. In the present embodiment, the electric-receiver-side resonator 25 is a resonance circuit in which an electric receiver coil 26 and an electric-receiver-side capacitor 27 are electrically connected in parallel relative to each other. By the electric-supplier-side resonator 21 resonating, a magnetic field occurs. At this time, a magnetic force is being emitted from the magnetic force emission surface 6A of the electric supplier unit 6. In the electric-receiver-side resonator 25, the inductance of the electric receiver coil 26 and the capacitance of the electric-receiver-side capacitor 27 are set in such a state that the electric-receiver-side resonator 25 electrically resonates at the same resonance frequency f0 as the electric-supplier-side resonator 21. Thus, by the magnetic field generated by the resonance of the electric-supplier-side resonator 21 being coupled to the electric receiver coil 26 of the electric-receiver-side resonator 25, the electric-receiver-side resonator (electric-receiver-side resonance circuit) 25 electrically resonates at the same resonance frequency (natural frequency) f0 as the electric-supplier-side resonator 21. Specifically, by the coupling between the magnetic field, which is generated by the resonance of the electric-supplier-side resonator 21, and the electric receiver coil 26, the electric-supplier-side resonator 21 and the electric-receiver-side resonator 25 resonate at the same resonance frequency f0. By the electric-supplier-side resonator 21 and the electric-receiver-side resonator 25 resonating at the same resonance frequency f0, the AC electric power (AC current) of the resonance frequency f0 is supplied from the electric supplier coil 22 to the electric receiver coil 26. The resonance frequency at a time when the electric-supplier-side resonator 21 and electric-receiver-side resonator 25 resonate is, for example, 13.56 MHz.

A contactless electric power transmission method, in which electric power is supplied from the electric supplier coil 22 to the electric receiver coil in the state in which the electric-supplier-side resonator 21 (electric supplier coil 22) and the electric-receiver-side resonator 25 (electric receiver coil 26) are not electrically connected (i.e. by wireless transmission) by utilizing, as described above, the resonance phenomenon in which the electric-supplier-side resonator 21 and electric-receiver-side resonator 25 resonate at the same resonance frequency f0, is called "electromagnetic field resonance method". As the contactless electric power transmission method in which electric power is supplied from the electric supplier coil 22 to the electric receiver coil in the state in which the electric supplier coil 22 and the electric receiver coil 26 are not electrically connected, there is known, aside from the electromagnetic field resonance method, an electromagnetic induction method in which electric power is supplied from the electric supplier coil 22 to the electric receiver coil 26 by utilizing electromagnetic induction between the electric supplier coil 22 and the electric receiver coil 26. In the electromagnetic field resonance method, compared to the electromagnetic induction method, even if the distance between the electric supplier coil 22 and the electric receiver coil 26 is large, electric power is supplied from the electric supplier coil 22 to electric receiver coil 26 at high efficiency. For example, if the distance from the energy treatment instrument 2 to the electric supplier unit 6 including the electric-supplier-side resonator 21 is several meters or less, electric power is supplied from the electric supplier coil 22 to electric receiver coil 26 at high efficiency.

In addition, in the electromagnetic field resonance method, the position and attitude of the energy treatment instrument 2 are adjusted in the state in which a coil axis L of the electric receiver coil 26 passes through the electric supplier unit 6 (electric-supplier-side resonator 21). Thereby, the sensitivity to the magnetic field in the electric receiver coil 26 is enhanced, and the magnetic field, which is generated by the resonance of the electric-supplier-side resonator 21, and the electric receiver coil 26 are coupled more easily. Thus, by adjusting the position and attitude of the energy treatment instrument 2 in the state in which the coil axis L of the electric receiver coil 26 passes through the electric supplier unit 6 (electric-supplier-side resonator 21), the supply efficiency of electric power from the electric supplier coil 22 to the electric receiver coil 26 is enhanced. In particular, by adjusting the position and attitude of the energy treatment instrument 2 in the state in which the coil axis L of the electric receiver coil 26 is perpendicularly cross to the magnetic force emission surface 6A of the electric supplier unit 6, the sensitivity to the magnetic field in the electric receiver coil 26 becomes maximum, and the magnetic field, which is generated by the resonance of the electric-supplier-side resonator 21, and the electric receiver coil 26 are coupled still more easily.

The energy treatment instrument 2 includes a converter circuit 31 which is electrically connected to the electric-receiver-side resonator 25. The converter circuit 31 includes a diode and a DC/DC converter, and rectifies AC electric power which has been supplied to the electric receiver coil 26. Thereby, the AC electric power (AC current) of the resonance frequency f0 is converted to DC electric power (DC current). In addition, the energy treatment instrument 2 includes a relay circuit 32 which is electrically connected to the converter circuit 31, a battery 33 which is an accumulator, a controller 35 which is electrically connected to the battery 33, and a storage such as a memory. The battery 33 is a magnetic member including a magnetic material. The controller 35 includes a processor, which includes a CPU (Central Processing Unit) or an ASIC (application specific integrated circuit); a clock signal generating circuit; and a protection circuit. In addition, the storage 36 stores, for example, a control program which is executed by the controller 35. Electric power is supplied from the battery 33 to the controller 35, and thereby a clock signal is generated by the clock signal generating circuit, and the controller 35 is activated. In addition, by being activated, the controller 35 executes control by the protection circuit in such a state that overcharge, over-discharge and overcurrent of the battery 33 are prevented. The relay circuit 32 is electrically connected to the battery 33 and controller 35, and the controller 35 controls the relay circuit 32.

The energy treatment instrument 2 includes an operation switch 37 which is electrically connected to the controller 35, and a driving circuit 38 which is an energy generator that is electrically connected to the relay circuit 32 and controller 35. The operation switch 37 is provided in the inside of the held unit 3, and the open state and closed state of the operation switch 37 are changed over based on an operation input in the energy operation input button 16. By detecting the open state or closed state of the operation switch 37, the controller 35 detects the input of the energy operation in the energy operation input button 16. In addition, based on the detection result of the input of the energy operation, the controller 35 controls the relay circuit 32 and driving circuit 38.

The relay circuit 32 includes a change-over switch 41. The change-over switch 41 includes electrical contact points X1 to X3. In the state in which the energy operation is not input by the energy operation input button 16, the controller 35 controls the change-over switch 41, thereby electrically connecting the electrical contact point X1 and electrical contact point X2. Thereby, the electric power, which has been received by the electric receiver coil 26 and has been converted to DC electric power by the converter circuit 31, is supplied to the battery 33, and the electric power is accumulated in the battery (accumulator) 33. On the other hand, in the state in which the energy operation is being input by the energy operation input button 16, the controller 35 controls the change-over switch 41, thereby electrically connecting the electrical contact point X1 and electrical contact point X3. Thereby, DC electric power is supplied from the battery 33 to the driving circuit 38, and the driving circuit 38 is driven.

The driving circuit 38 includes a converter circuit which converts the DC electric power to vibration generating electric power (AC electric power) for generating ultrasonic vibration, and a converter circuit which converts the DC electric power to high-frequency electric power. In the state in which the energy operation is being input, the controller 35 controls the driving circuit 38, thereby converting the DC electric power, which is supplied from the battery 33, to vibration generating electric power and high-frequency electric power, and outputting the vibration generating electric power and high-frequency electric power from the driving circuit 38. Accordingly, by using the electric power which is supplied from the electric supplier coil 22 to the electric receiver coil 26, the driving circuit (energy generator) 38 generates energy (vibration generating electric power and high-frequency electric power) which is used in a treatment.

The driving circuit 38 is electrically connected via electrical paths 42A and 42B to an ultrasonic transducer 43 which is a vibration generator that is disposed in the inside of the held unit 3. By the vibration generating electric power being supplied from the driving circuit 36 to the ultrasonic transducer 43, ultrasonic vibration occurs in the ultrasonic transducer 43. In addition, the driving circuit 38 is electrically connected to the treatment portion 17 of the vibration transmitter 8 via an electrical path 45A, and is electrically connected to the jaw 18 via an electrical path 45B. By the high-frequency electric power being supplied from the driving circuit 38 to the treatment portion 17 and jaw 18, the treatment portion 17 and jaw 18 function as electrodes of high-frequency electric powers with mutually different electric potentials.

Figure 3:
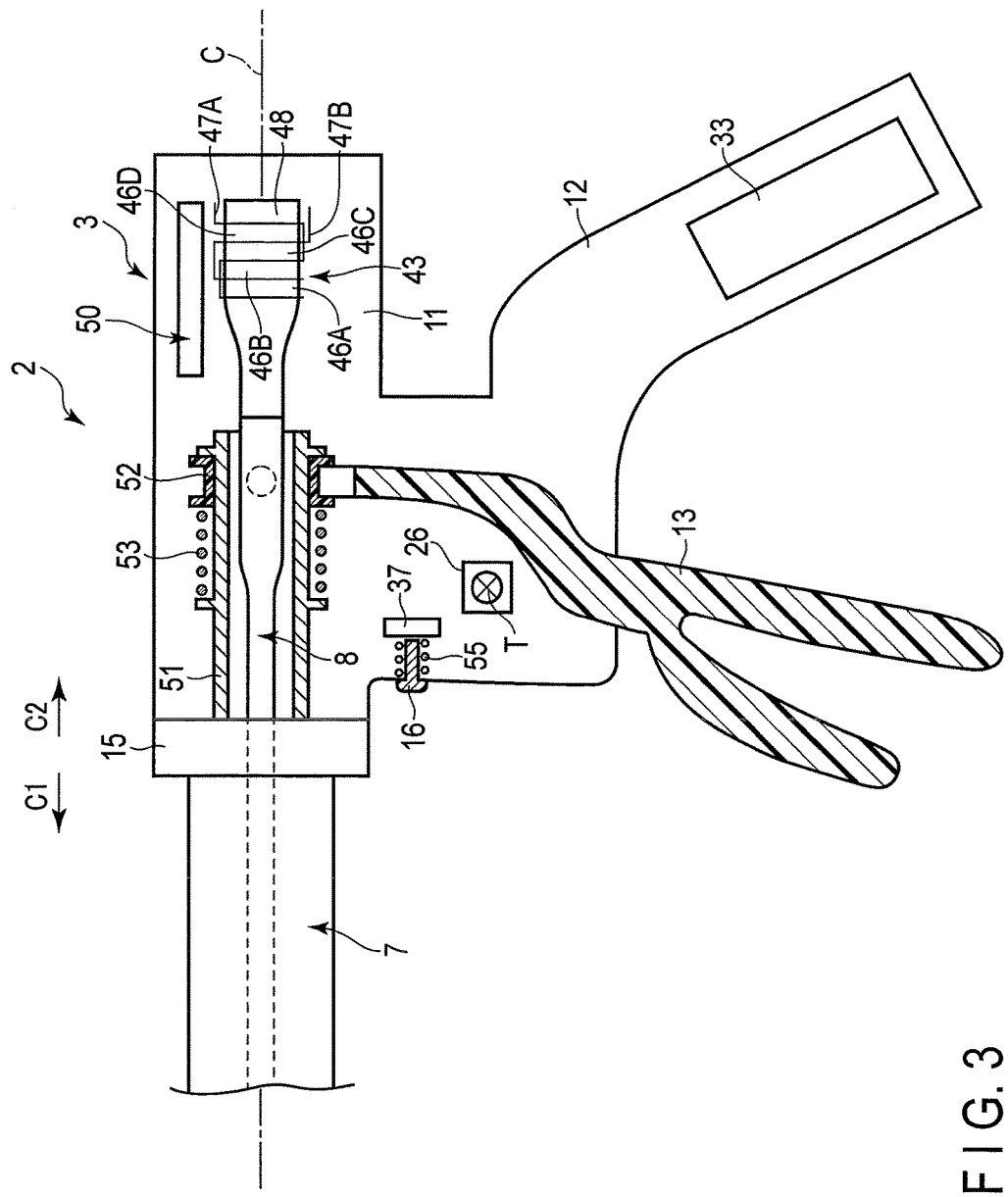
FIG. 3 is a schematic view illustrating an internal configuration of a held unit according to the first embodiment, by a cross section perpendicular to a width direction of the held unit.

FIG. 3 is a view which schematically illustrates an internal configuration of the held unit 3. FIG. 3 illustrates a cross section perpendicular to the width direction of the held unit 3. As illustrated in FIG. 3, the ultrasonic transducer 43 is coupled to a proximal portion of the vibration transmitter 8 in the inside of the case main body 11, and extends along the longitudinal axis C, with the axial center thereof substantially agreeing with the longitudinal axis C. The ultrasonic vibration, which is generated in the ultrasonic transducer 43, is transmitted to the treatment portion 17 from the proximal side toward the distal side in the vibration transmitter 8. The ultrasonic transducer 43 includes piezoelectric elements 46A to 46D which convert AC current (vibration generating current) to vibration; electrode members 47A and 47B which apply a voltage to the piezoelectric elements 46A to 46D; and a back-mass 48 which holds the piezoelectric elements 46A to 46D between the back-mass 48 and the vibration transmitter 8 in a direction along the longitudinal axis C. The electrode members 47A and 47B are formed of a magnetic material such as stainless steel. In addition, the back-mass 48 may be formed of a non-magnetic material such as duralumin, titanium or copper, or may be formed of a magnetic material such as stainless steel. Accordingly, the ultrasonic transducer 43 is a magnetic member including a magnetic material.

Besides, a circuit unit 50 is disposed in the inside of the case main body 11. The circuit unit 50 is composed of the above-described converter circuit 31, relay circuit 32, controller 35 and driving circuit 38. In the present embodiment, the circuit unit 50 is located on a side opposite to the stationary handle 12 and movable handle 13 with respect to the longitudinal axis C. In the circuit unit 50, fixing screws which fix the above-described circuits to a board, and a voltage transformer such as a DC/DC converter included in the above-described circuits, are formed of a magnetic material. Accordingly, the circuit unit 50 is a magnetic member including a magnetic material.

In addition, the sheath 7 includes a movable cylindrical portion 51 which extends from the inside of the case main body 11 toward the distal side along the longitudinal axis C. A cylindrical slider member 52 is provided on an outer peripheral surface of the movable cylindrical portion 51, and the movable handle 13 is coupled to the slider member 52 in the inside of the case main body 11. In addition, a cylindrical elastic member 53 is provided on the outer peripheral surface of the movable cylindrical portion 51, the elastic member 53 extending along the longitudinal axis C, with the axial center thereof substantially agreeing with the longitudinal axis C. One end (proximal end) of the elastic member 53 is connected to the slider member 52, and the other end (distal end) of the elastic member 53 is connected to the movable cylindrical portion 51. In the present embodiment, in the inside of the case main body 11, the slider member 52 and elastic member 53 are located on the distal side with respect to the ultrasonic transducer 43 and circuit unit 50.

By closing the movable handle 13 relative to the stationary handle 12, the slider member 52, the elastic member 53, and the movable cylindrical portion 52 of the sheath 7 move toward the distal side, and the jaw 18 closes relative to the treatment portion 17. In addition, by the jaw 18 abutting on the grasped treated target and by the treated target being compressed to some degree, the slider member 52 moves toward the distal side relative to the movable cylindrical portion 51, and the elastic member 53 contracts. Specifically, by closing the movable handle 13 relative to the stationary handle 12, the elastic member 53 contracts. By the elastic member 53 contracting, the grasping force between the treatment portion 17 and jaw 18 increases. The elastic member 53 is a magnetic member including a magnetic material.

In addition, in the inside of the stationary handle 12, the above-described battery 33 is disposed, and the above-described operation switch 37 is disposed at such a position that the operation switch 37 can be pushed by the energy operation input button 16. In the present embodiment, compared to the operation switch 37, the battery 33 is located more distant from the case main body 11 (longitudinal axis C). Furthermore, an urging member 55 is attached to the stationary handle 12, and the energy operation input button 16 is urged by the urging member 55 to a position where the operation switch 37 is not pushed (i.e. a position where the operation switch 37 is set in the open state). Since the urging member 55 includes, for example, iron, the urging member 55 is a magnetic member which is formed of a magnetic material.

FIG. 4 is a view illustrating the internal configuration of the held unit 3 by a cross section perpendicular to the longitudinal axis C which passes through the electric receiver coil 26. As illustrated in FIG. 3 and FIG. 4, the electric receiver coil 26 is disposed in the inside of the stationary handle 12. In the present embodiment, compared to the electric receiver coil 26, the battery 33 is located more distant from the case main body 11 (longitudinal axis C). In the inside of the stationary handle 12, the electric receiver coil 26 is located between the battery 33 and the operation switch 37. The electric receiver coil 26 is helically wound around a coil axis T. In this embodiment, the coil axis T of the electric receiver coil 26 extends substantially parallel to the width direction of the held unit 3 (directions of an arrow W1 and an arrow W2 in FIG. 4). Thus, the coil axis T of the electric receiver coil 26 extends substantially perpendicular to a cross section which is perpendicular to the width direction of the held unit 3 shown in FIG. 3. Incidentally, the coil axis T is an imaginary axis which extends also in a region where the coil 26 is not wound (e.g. an outside of the energy treatment instrument 2).

In the cross section shown in FIG. 3, the coil axis T of the electric receiver coil 26 passes through a position which is distant from each of the above-described magnetic members (sheath 7, jaw 18, battery 33, ultrasonic transducer 43, elastic member 53 and urging member 55 etc.). Thus, in a projection from each of one side (an arrow W1 side in FIG. 4) and the other side (an arrow W2 side in FIG. 4) of the width direction of the held unit 3, the coil axis T of the electric receiver coil 26 passes through a position which is distant from the above-described magnetic members (7, 18, 33, 43, 50, 53, 55). Accordingly, in all cross sections perpendicular to the width direction of the held unit 3, the coil axis T of the electric receiver coil 26 passes through a position which is apart from the above-described magnetic members (7, 18, 33, 43, 50, 53, 55).

In addition, the electric receiver coil 26 is located in the inside of the stationary handle 12, and the coil axis T of the electric receiver coil 26 is substantially parallel to the width direction of the held unit 3. Thus, in the cross section perpendicular to the longitudinal axis C shown in FIG. 4, the coil axis T of the electric receiver coil 26 passes through a position which is more distant from the longitudinal axis C than an outer peripheral surface of the elastic member 53. Specifically, in the cross section shown in FIG. 4, the coil axis T of the electric receiver coil 26 passes through a position which is more apart from the longitudinal axis C than the outer peripheral surface of the elastic member 53 which is a magnetic member that extends along the longitudinal axis C, with the axial center thereof substantially agreeing with the longitudinal axis C. Accordingly, in a projection from each of one side and the other side (distal side and proximal side) of the direction along the longitudinal axis C, the coil axis T of the electric receiver coil 26 passes through a position which is more distant from the longitudinal axis C than the outer peripheral surface of the elastic member 53. Similarly, in a projection from each of one side and the other side of the direction along (parallel to) the longitudinal axis C, the coil axis T of the electric receiver coil 26 passes through a position which is more distant from the longitudinal axis C than the outer peripheral surface of each of the sheath 7 and ultrasonic transducer 43 which are other magnetic members that extend along the longitudinal axis C, with the axial centers thereof substantially agreeing with the longitudinal axis C.

In addition, in the cross section shown in FIG. 4, which is perpendicular to the longitudinal axis C, the coil axis T of the electric receiver coil 26 passes through a position which is distant from the above-described magnetic members (7, 18, 33, 43, 50, 53, 55). Besides, in a projection from each of one side and the other side of the direction along the longitudinal axis C, the coil axis T of the electric receiver coil 26 passes through a position which is distant from the above-described magnetic members (7, 18, 33, 43, 50, 53, 55). Accordingly, in all cross sections perpendicular to the longitudinal axis C, the coil axis T of the electric receiver coil 26 passes through a position which is distant from the above-described magnetic members (7, 18, 33, 43, 50, 53, 55).

Because of the above-described configuration, in the energy treatment instrument 2, the coil axis T of the electric receiver coil 26 passes through a position which is distant from the above-described magnetic members (7, 18, 33, 43, 50, 53, 55), and each of the magnetic members (7, 18, 33, 43, 50, 53, 55) is located distant from the coil axis T of the electric receiver coil 26. Specifically, the coil axis T of the electric receiver coil 26 extends in the state in which the coil axis T passes through none of the magnetic members (7, 18, 33, 43, 50, 53, 55).

Next, the functions and advantageous effects of the energy treatment instrument 2 and energy treatment system 1 of the present invention will be described. When a treatment is performed by using the energy treatment system 1, DC electric power is supplied from the electric power source 5 to the electric-supplier-side resonator 21 of the electric supplier unit 6, and the electric-supplier-side resonator 21 is caused to electrically resonate. Then, the magnetic field, which is generated by the resonance of the electric-supplier-side resonator 21, and the electric receiver coil 26 are coupled, and the electric-receiver-side resonator 25 resonates at the same resonance frequency f0 as the electric-supplier-side resonator 21. By the electric-supplier-side resonator 21 and the electric-receiver-side resonator 25 resonating at the same resonance frequency f0, AC electric power (AC current) of the resonance frequency f0 is supplied from the electric supplier coil 22 to the electric receiver coil 26. At this time, without the electric-supplier-side resonator 21 and the electric-receiver-side resonator 25 being electrically connected (i.e. by wireless transmission), the electric receiver coil 26 receives electric power from the electric supplier coil 22. In the state in which the energy operation is not input by the energy operation input button 16, the electrical contact point X1 and electrical contact point X2 in the change-over switch 41 of the relay circuit 32 are electrically connected by the control of the controller 35. Thus, the electric power, which has been received by the electric receiver coil 26, is converted to DC electric power by the converter circuit 31, and the DC electric power is accumulated in the battery 33.

In the treatment, the sheath 7, the treatment portion 17 of the vibration transmitter 8, and the jaw 18 are inserted into a body cavity through the hole of the trocar which is fixed to the body wall. Then, a treatment target, such as a biological tissue, is disposed between the treatment portion 17 and the jaw 18, and the movable handle 13 is closed relative to the stationary handle 12. Thereby, the jaw 18 is closed relative to the treatment portion 17, and the treated target is grasped between the treatment portion 17 and the jaw 18. At this time, the elastic member 53 contracts, and the grasping force between treatment portion 17 and jaw 18 increases.

In the state in which the treated target is grasped between the treatment portion 17 and jaw 18, an energy operation is input by the energy operation input button 16. When the controller 35 has detected the input of the energy operation, the electrical contact point X1 and electrical contact point X3 in the change-over switch 41 of the relay circuit 32 are electrically connected by the control of the controller 35. Thereby, DC electric power is supplied from the battery 33 to the driving circuit 38, and energy for use in the treatment is generated in the driving circuit (energy generator) 38. Specifically, the driving circuit 38 generates vibration generating electric power and high-frequency electric power by using the electric power which is supplied to the electric receiver coil 26.

By the vibration generating electric power being supplied from the driving circuit 38 to the ultrasonic transducer 43, ultrasonic vibration is generated by the ultrasonic transducer 43. Then, the generated ultrasonic vibration is transmitted to the treatment portion 17 from the proximal side toward the distal side in the vibration transmitter 8. In the state in which the treated target is grasped between the treatment portion 17 and jaw 18, the treatment portion 17 vibrates by ultrasonic vibration. Thereby, the treated target is cut and open and, at the same time, coagulated by frictional heat between the treatment portion 17 and the treated target. In addition, by the high-frequency energy (high-frequency electric power) being supplied from the driving circuit 38 to the treatment portion 17 and jaw 18, the treatment portion 17 and jaw 18 function as high-frequency electrodes. In the state in which the treated target is grasped between the treatment portion 17 and jaw 18, a bipolar treatment is performed with the treatment portion 17 and jaw 18 functioning as the electrodes. Thereby, a high-frequency current flows through the treated target between the treatment portion 17 and jaw 18. By the high-frequency current flowing through the treated target, the coagulation of the treated target is promoted.

In the present embodiment, the coil axis T of the electric receiver coil 26 passes through a position which is distant from the above-described magnetic members (sheath 7, jaw 18, battery 33, ultrasonic transducer 43, elastic member 53 and urging member 55 etc.), and each of the magnetic members (7, 18, 33, 43, 50, 53, 55) is located distant from the coil axis T of the electric receiver coil 26. Thus, the magnetic field, which is generated by the resonance of the electric-supplier-side resonator 21, is effectively prevented from being shielded by the magnetic members (7, 18, 33, 43, 50, 53, 55) before the magnetic field is coupled to the electric receiver coil 26. Since the magnetic members (7, 18, 33, 43, 50, 53, 55) are not located on the coil axis T of the electric receiver coil 26 and in the vicinity thereof, the electric receiver coil 26 is properly coupled to the magnetic field generated by the resonance of the electric-supplier-side resonator 21. Thereby, by the electric-supplier-side resonator 21 electrically resonating, the electric-supplier-side resonator 21 and the electric-receiver-side resonator 25 properly resonate at the same resonance frequency f0. Accordingly, electric power is properly supplied from the electric supplier coil 22 to the electric receiver coil 26 by the electromagnetic field resonance method (by wireless transmission), and the transmission efficiency of electric power from the electric supplier coil 22 to electric receiver coil 26 can be secured. Since the transmission efficiency of electric power from the electric supplier coil 22 to electric receiver coil 26 is secured, the supply efficiency of energy for use in the treatment, which is supplied from the driving circuit 38, can also be secured.

Besides, in the treatment, although the held unit 3 is held by the hand of the surgeon, the principal component of the bone of the hand is calcium phosphate, and is a non-magnetic material. In fact, the magnetic permeability of the bone is about $1.256627 \times 10^{-6}$ [H/m], and is substantially equal to the magnetic permeability ($1.256637 \times 10^{-6}$ [H/m]) of air. Thus, even if the held unit 3 is held by the hand of the surgeon, the magnetic field, which is generated by the resonance of the electric-supplier-side resonator 21, is not shielded by the hand, and the electric receiver coil 26 is properly coupled to the magnetic field. Therefore, even in the state in which the held unit 3 is held by the hand of the surgeon, the transmission efficiency of electric power from the electric supplier coil 22 to electric receiver coil 26 can be secured.

(Modifications)

Figure 6:
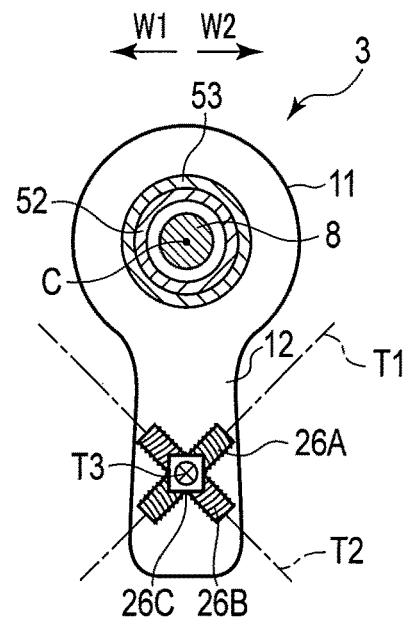
FIG. 6 is a schematic view illustrating the internal configuration of the held unit according to the first modification, by a cross section perpendicular to a longitudinal axis which passes through an electric receiver coil.
Figure 7:
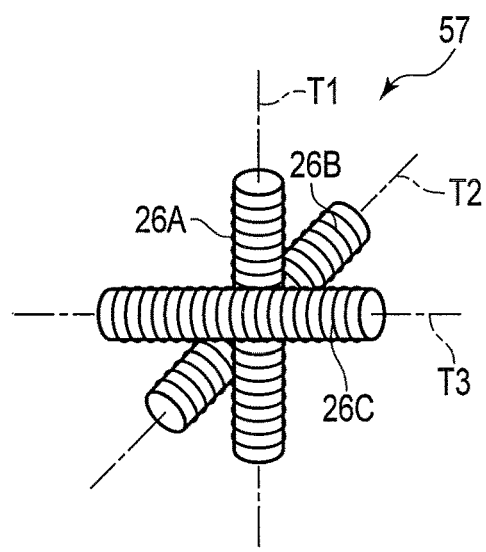
FIG. 7 is a perspective view which schematically illustrates a bar antenna which is formed by the electric receiver coil according to the first modification.

In the meantime, in the first embodiment, only one electric receiver coil 26 is provided, but the restriction to this is unnecessary. For example, as illustrated in FIG. 5 to FIG. 7 as a first modification, a plurality (three in this modification) of electric receiver coils 26A to 26C may be provided. Each of the electric receiver coils 26A to 26C is wound around the corresponding coil axis (corresponding one of T1 to T3). The extending direction of the coil axis (corresponding one of T1 to T3) of each of the electric receiver coils 26A to 26C is different from the extending directions of the coil axes (corresponding two of T1 to T3) of the other electric receiver coils (corresponding two of 26A to 26C). For example, the extending direction of the coil axis T1 of the electric receiver coil 26A is different from the extending directions of the coil axes T2 and T3 of the other electric receiver coils 26B and 26C. As illustrated in FIG. 7, in the present modification, a bar antenna 57 is formed by the three electric receiver coils 26A to 26C. Incidentally, each of the coil axes T1 to T3 is an imaginary axis which extends also in a region where the corresponding electric receiver coil (corresponding one of 26A to 26C) is not wound.

In the present modification, in a cross section (e.g. a cross section shown in FIG. 5) which is perpendicular to the width direction of the held unit 3 (directions of an arrow W1 and an arrow W2 in FIG. 6), each of the coil axes T1 to T3 of the electric receiver coils 26A to 26C passes through a position which is distant from the magnetic members (sheath 7, jaw 18, battery 33, ultrasonic transducer 43, elastic member 53 and urging member 55 etc.). Thus, in a projection from each of one side and the other side of the width direction of the held unit 3, each of the coil axes T1 to T3 of the electric receiver coils 26A to 26C passes through a position which is distant from the above-described magnetic members (7, 18, 33, 43, 50, 53, 55).

In addition, in the present modification, in the cross section perpendicular to the longitudinal axis C shown in FIG. 6, each of the coil axes T1 to T3 of the electric receiver coils 26A to 26C passes through a position which is more distant from the longitudinal axis C than the outer peripheral surface of the elastic member 53. Accordingly, in a projection from each of one side and the other side (distal side and proximal side) of the direction along the longitudinal axis C, each of the coil axes T1 to T3 of the electric receiver coils 26A to 26C passes through a position which is more distant from the longitudinal axis C than the outer peripheral surface of the elastic member 53. Similarly, in a projection from each of one side and the other side of the direction along (parallel to) the longitudinal axis C, each of the coil axes T1 to T3 of the electric receiver coils 26A to 26C passes through a position which is more distant from the longitudinal axis C than the outer peripheral surface of each of the sheath 7 and ultrasonic transducer 43 which are other magnetic members that extend along the longitudinal axis C, with the axial centers thereof substantially agreeing with the longitudinal axis C.

In addition, in the cross section shown in FIG. 6, which is perpendicular to the longitudinal axis C, each of the coil axes T1 to T3 of the electric receiver coils 26A to 26C passes through a position which is distant from the above-described magnetic members (7, 18, 33, 43, 50, 53, 55). Besides, in a projection from each of one side and the other side of the direction along the longitudinal axis C, each of the coil axes T1 to T3 of the electric receiver coils 26A to 26C passes through a position which is apart from the magnetic members (7, 18, 33, 43, 50, 53, 55).

Because of the above-described configuration, in the present modification, in the energy treatment instrument 2, each of the coil axes T1 to T3 of the electric receiver coils 26A to 26C passes through a position which is distant from the above-described magnetic members (7, 18, 33, 43, 50, 53, 55), and each of the magnetic members (7, 18, 33, 43, 50, 53, 55) is located distant from the coil axes T1 to T3 of the electric receiver coils 26A to 26C. Specifically, each of the coil axes T1 to T3 of the electric receiver coils 26A to 26C extends in the state in which each of the coil axes T1 to T3 passes through none of the magnetic members (7, 18, 33, 43, 50, 53, 55).

Accordingly, also in the present modification, the magnetic field, which is generated by the resonance of the electric-supplier-side resonator 21, is effectively prevented from being shielded by the magnetic members (7, 18, 33, 43, 50, 53, 55) before the magnetic field is coupled to each of the electric receiver coils 26A to 26C. Specifically, since the magnetic members (7, 18, 33, 43, 50, 53, 55) are not located on the coil axis (corresponding one of T1 to T3) of each of the electric receiver coils 26A to 26C and in the vicinity thereof, each of the electric receiver coils 26A to 26C is properly coupled to the magnetic field generated by the resonance of the electric-supplier-side resonator 21. Accordingly, electric power is properly supplied from the electric supplier coil 22 to each of the electric receiver coils 26A to 26C by the electromagnetic field resonance method (by wireless transmission), and the transmission efficiency of electric power from the electric supplier coil 22 to each of the electric receiver coils 26A to 26C can be secured.

In addition, in the present modification, the extending direction of the coil axis (corresponding one of T1 to T3) of each of the electric receiver coils 26A to 26C is different from the extending directions of the coil axes (corresponding two of T1 to T3) of the other electric receiver coils (corresponding two of 26A to 26C). Thus, even when the coil axis (T1) of one electric receiver coil (e.g. 26A) does not pass through the electric supplier unit 6, the energy treatment instrument 2 may be adjusted in such a position and attitude that the coil axis (T2) of at least one (e.g. 26B) of the other electric receiver coils (26B, 26C) passes through the electric supplier unit 6, and thereby the sensitivity to the magnetic field in the electric receiver coil (26B), the coil axis (T2) of which passes through the electric supplier unit 6, increases. Specifically, although the sensitivity to the magnetic field in the electric receiver coil (26A), the coil axis (T1) of which does not pass through the electric supplier unit 6, decreases, the sensitivity to the magnetic field in the electric receiver coil (26B), the coil axis (T2) of which passes through the electric supplier unit 6, increases, thus complementing the sensitivity to the magnetic field. Accordingly, in each of various positions and attitudes in which the energy treatment instrument 2 is used, the coil axis (T2) of at least one (e.g. 26B) of the electric receiver coils 26A to 26C passes through the electric supplier unit 6, and the sensitivity to the magnetic field in the electric receiver coil (26B), the coil axis (T2) of which passes through the electric supplier unit 6, increases. Thus, in each of various positions and attitudes in which the energy treatment instrument 2 is used, the electric receiver coil (e.g. 26B), in which the sensitivity to the magnetic field increases, is properly coupled to the magnetic field generated by the resonance of the electric-supplier-side resonator 21. Accordingly, in each of various positions and attitudes in which the energy treatment instrument 2 is used, the supply efficiency of electric power from the electric supplier coil 22 to at least one (e.g. 26B) of the electric receiver coils 26A to 26C is secured. Thereby, even when the position and attitude of the energy treatment instrument have changed, electric power is stably supplied from the electric supplier coil 22 to any one of the electric receiver coils 26A to 26C.

In the meantime, when a plurality of electric receiver coils (e.g. 26A to 26C) are provided, it should suffice if such a configuration is adopted that the extending direction of the coil axis (e.g. corresponding one of T1 to T3) of each of the electric receiver coils (e.g. 26A to 26C) is different from the extending direction of the coil axis (e.g. at least one of T1 to T3) of at least one of the other electric receiver coils (e.g. corresponding two of 26A to 26C). Thereby, compared to the case in which the number of electric receiver coils (26) is one, the magnetic field, which is generated by the resonance of the electric-supplier-side resonator 21, and any of the electric receiver coils (e.g. 26A to 26C), are coupled more easily.

Besides, when a plurality of electric receiver coils (26A to 26C) are provided, the plural electric receiver coils (26A to 26C) may be disposed in one electric-receiver-side resonator (electric-receiver-side resonance circuit) 25. In addition, a plurality of electric-receiver-side resonators (electric-receiver-side resonance circuits) 25 may be provided, and each of the plural electric receiver coils (26A to 26C) may be disposed in the corresponding electric-receiver-side resonator 25. When a plurality of electric-receiver-side resonators 25 are provided, each of the plural electric-receiver-side resonators 25 is electrically connected to the converter circuit 31, and the converter circuit 31 converts AC electric power, which has been received by each of the electric-receiver-side resonators 25, to DC electric power which can be accumulated in the battery 33.

Additionally, in a second modification illustrated in FIG. 8, a loop antenna 58 is formed by a plurality (three in this modification) of electric receiver coils 26A to 26C. Compared to the bar antenna (57), the loop antenna 58 has a greater cross-sectional area perpendicular to the coil axis (corresponding one of T1 to T3) of each of the electric receiver coils 26A to 26C. Thus, in the loop antenna 58, the sensitivity to the magnetic field in each of the electric receiver coils 26A to 26C increases. Accordingly, the supply efficiency of electric power from the electric supplier coil 22 to each of the electric receiver coils 26A to 26C is enhanced.

Additionally, the relay circuit 32 is not restricted to the configuration of the first embodiment. For example, in a third modification illustrated in FIG. 9, the relay circuit 32 is provided with two change-over switches 41A and 41B and two diodes 61A and 61B. The change-over switch 41A includes electrical contact points X1 to X3, and the change-over switch 41B includes electrical contact points Y1 and Y2. In the state in which the energy operation is not input by the energy operation input button 16, the controller 35 controls the change-over switch 41A, thereby electrically connecting the electrical contact point X1 and electrical contact point X2. In addition, the controller 35 controls the change-over switch 41B, thereby setting the change-over switch 41B in the open state. Thereby, the electric power, which has been received by the electric receiver coil 26 and has been converted to DC electric power by the converter circuit 31, is accumulated in the battery (accumulator) 33.

In the state in which the energy operation is being input by the energy operation input button 16, the controller 35 controls the change-over switches 41A and 41B in accordance with the magnitude of electric power which is necessary for generating energy by the driving circuit 38. When the electric power, which is necessary for generating energy by the driving circuit 38, is not greater than the electric power supplied from the converter circuit 31, the controller 35 controls the change-over switch 41A, thereby setting the change-over switch 41A in the open state. In addition, the controller 35 controls the change-over switch 41B, thereby setting the change-over switch 41B in the closed state and electrically connecting the electrical contact point Y1 and electrical contact point Y2. Thereby, the electric power, which has been received by the electric receiver coil 26 and has been converted to DC electric power by the converter circuit 31, is directly supplied to the driving circuit 38. On the other hand, when the electric power, which is necessary for generating energy by the driving circuit 38, is greater than the electric power supplied from the converter circuit 31, the controller 35 controls the change-over switch 41A, thereby electrically connecting the electrical contact point X1 and electrical contact point X3 in the switch 41A. In addition, the controller 35 controls the change-over switch 41B, thereby setting the change-over switch 41B in the closed state and electrically connecting the electrical contact point Y1 and electrical contact point Y2. Thereby, the electric power, which has been received by the electric receiver coil 26 and has been converted to DC electric power by the converter circuit 31, is directly supplied to the driving circuit 38, and also the electric power accumulated in the battery 33 is supplied to the driving circuit 38.

As described above, in the present modification, even in the treatment in which the electric power, which is necessary for generating energy by the driving circuit 38, becomes greater than the electric power supplied from the converter circuit (the electric power received by the electric receiver coil 26), the electric power of the required magnitude can be supplied to the driving circuit 38. In the meantime, in the state in which electric power is supplied from both the converter circuit 31 (electric receiver coil 26) and the battery 33, a reverse flow of electric current is prevented by the diodes 61A and 61B when the voltage of electric power from the converter circuit 31 and the voltage of electric power from the battery 33 are different.

Figure 10:
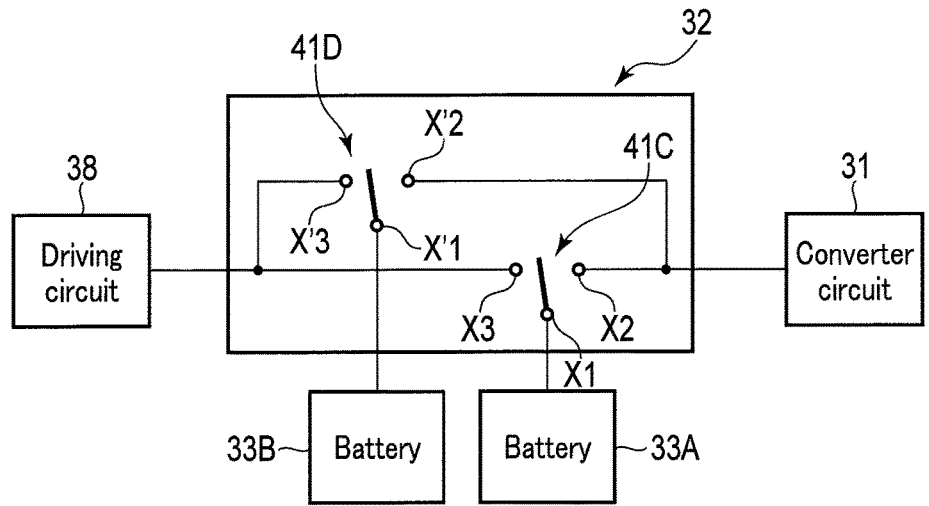
FIG. 10 is a schematic view illustrating a configuration of a relay circuit according to a fourth modification.

Additionally, in a fourth modification illustrated in FIG. 10, the relay circuit 32 is provided with two change-over switches 41C and 41D, and the energy treatment instrument 2 includes two batteries 33A and 33B. The change-over switch 41C includes electrical contact points X1 to X3, and the change-over switch 14D includes electrical contact points X'1 to X'3. In the present modification, based on the residual charge amounts of the batteries 33A and 33B, the controller 35 controls the change-over switches 41C and 41D. In the state in which the energy operation is not input by the energy operation input button 16, the controller 35 controls the change-over switches 41C and 41D, thereby supplying electric power from the converter circuit 31 to that one of the batteries 33A and 33B, which is less in residual charge amount. For example, in the state in which the energy operation is not input by the energy operation input button 16, when the residual charge amount of the battery 33A is less than the residual charge amount of the battery 33B, the electrical contact point X1 and electrical contact point X2 are electrically connected in the switch 41C, and the change-over switch 41D is controlled and set in the open state. Thereby, the electric power, which has been received by the electric receiver coil 26 and has been converted to DC electric power by the converter circuit 31, is accumulated in the battery (accumulator) 33A which is less in residual charge amount.

Besides, in the state in which the energy operation is being input by the energy operation input button 16, the controller 35 controls the change-over switches 41C and 41D, thereby supplying electric power from the converter circuit 31 to one of the batteries 33A and 33B, which is less in residual charge amount, and also supplying electric power from the battery 33A, 33B, which is greater in residual charge amount, to the driving circuit 38. For example, in the state in which the energy operation is being input by the energy operation input button 16, when the residual charge amount of the battery 33B is less than the residual charge amount of the battery 33A, the electrical contact point X1 and electrical contact point X3 are electrically connected in the switch 41C, and the change-over switch 41D is controlled and, thereby, the electrical contact point X'1 and electrical contact point X'2 are electrically connected. Thereby, the electric power, which has been received by the electric receiver coil 26 and has been converted to DC electric power by the converter circuit 31, is accumulated in the battery (accumulator) 33B which is less in residual charge amount. In addition, energy is supplied from the battery 33A, which is greater in residual charge amount, to the driving circuit 38, and the energy for use in the treatment is generated by the driving circuit 38.

As described above, in the present modification, even when the energy for use in the treatment is generated by the driving circuit 38 and the treatment is being performed, one of the batteries 33A and 33B, which does not supply electric power to the driving circuit 38, is charged.

Figure 11:
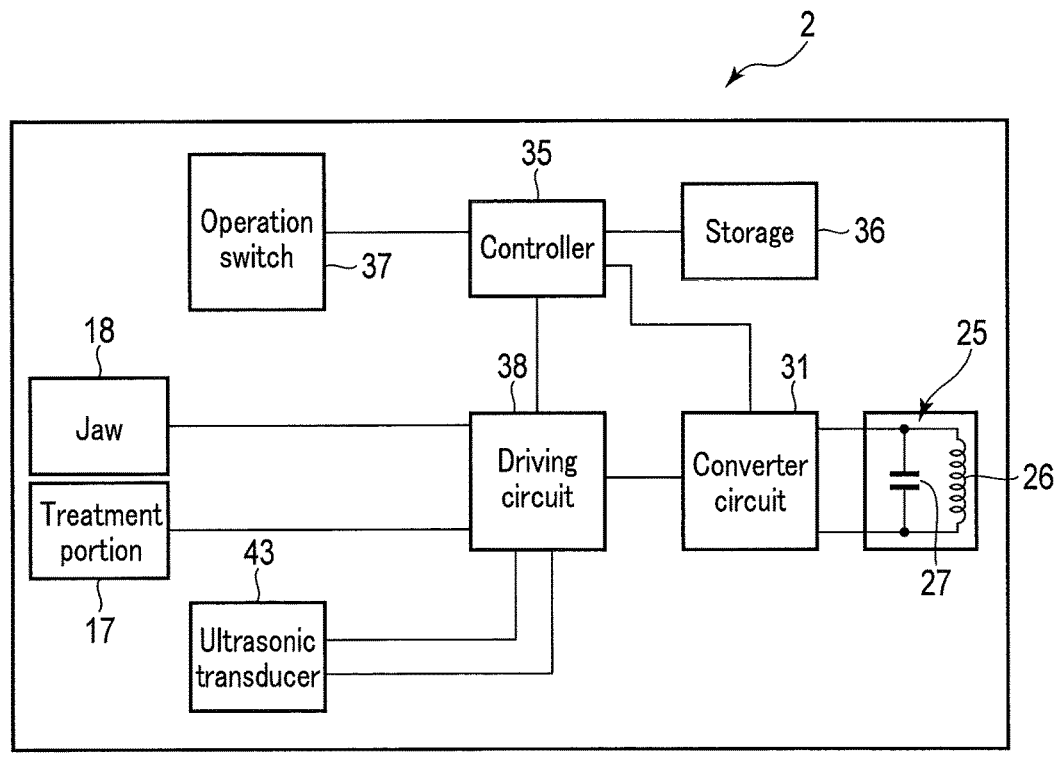
FIG. 11 is a schematic view illustrating a configuration which generates energy for use in a treatment in an energy treatment system according to a fifth modification.

Additionally, in a fifth modification illustrated in FIG. 11, the relay circuit 32 and battery 33 are not provided in the energy treatment instrument 2. In the present modification, the converter circuit 31 is electrically connected to the driving circuit 38 without intervention of the relay circuit (32), and is electrically connected to the controller 35. In this modification, the converter circuit 31 converts the electric power, which the electric receiver coil 26 has received, to electric power for generating a clock signal, and supplies the converted electric power to the controller 35. Thereby, the clock signal is generated by the clock signal generating circuit, and the controller 35 is activated. In addition, in the present modification, the electric power, which the electric receiver coil 26 has received, is converted to DC electric power by the converter circuit 31, and the DC electric power is supplied to the driving circuit 38. Thereby, energy (vibration generating electric power and high-frequency electric power) for use in the treatment is generated in the driving circuit 38.

In the meantime, the electric power, which the electric receiver coil 26 has received, may not be converted to DC electric power in the converter circuit 31, and AC electric power may be supplied to the driving circuit 38. In this case, an AC/AC converter or the like is provided in the driving circuit 38, and the energy (vibration generating electric power and high-frequency electric power) for use in the treatment is generated in the driving circuit 38 by using the supplied AC electric power.

Additionally, although the first embodiment relates to the energy treatment instrument 2 which grasps the treated target between the treatment portion 17 and jaw 18 that are inserted in the body cavity, the above-described configuration can be applied to an energy treatment instrument which is different in kind from the energy treatment instrument 2. For example, in an energy treatment instrument (handpiece) 70 of a sixth modification illustrated in FIG. 12, the jaw 18 is not provided, and the stationary handle 12, movable handle 13 and rotary operation knob 15 are not provided in the held unit (housing) 3. In addition, the slider member 52 and elastic member 53 are not provided in the energy treatment instrument 70. FIG. 12 illustrates the inside of the held unit 3 by a cross section perpendicular to the width direction of the held unit 3. In the present modification, a transducer case 71 is coupled to the case main body 11 of the held unit 3 from the proximal side, and the ultrasonic transducer 43 is disposed in the inside of the transducer case 71. By the transducer case 71 being coupled to the case main body 11, the ultrasonic transducer 43 is coupled to the proximal portion of the vibration transmitter 8. Also in this modification, the sheath 7, vibration transmitter 8, case main body 11 and ultrasonic transducer 43 extend along the longitudinal axis C, with the axial centers thereof substantially agreeing with the longitudinal axis C. Furthermore, also in this modification, the ultrasonic transducer 43 and sheath 7 are magnetic members including a magnetic material such as iron.

Also in the present modification, vibration generating electric power is supplied from the driving circuit 38 to the ultrasonic transducer 43, and ultrasonic vibration is generated by the ultrasonic transducer 43. In addition, the generated ultrasonic vibration is transmitted to the treatment portion 17 through the vibration transmitter 8. A treated target is abraded by the ultrasonic vibration being transmitted to the treatment portion 17 in the state in which the treatment portion 17 is put in contact with the treated target. At this time, in the driving circuit 38, high-frequency electric power is generated, and the high-frequency electric power is supplied to the treatment portion 17 at the same time as the transmission of the ultrasonic vibration.

Also in this modification, the circuit unit 50, which includes the converter circuit 31, controller 35 and driving circuit 38, is disposed in the inside of the case main body 11. Like the first embodiment, the circuit unit 50 is a magnetic member including a magnetic material. In addition, in the present modification, the energy operation input button 16 is attached to the case main body 11, and the operation switch 37, the open state and closed state of which are changed over based on the input of the energy operation in the energy operation input button 16, is provided in the inside of the case main body 11. Besides, the energy operation input button 16 is urged by the urging member 55 to a position where the operation switch 37 is not pushed (i.e. a position where the operation switch 37 is set in the open state). Also in this modification, the urging member 55 is a magnetic member which is formed of a magnetic material. In this modification, the energy operation input button 16, operation switch 37 and urging member 55 are located on the side opposite to the circuit unit 50 with respect to the longitudinal axis C.

In the present modification, the electric receiver coil 26 is provided in the inside of the case main body 11. The electric receiver coil 26 is located on the proximal side with respect to the circuit unit 50 and urging member 55 (energy operation input button 16), and is located on the side opposite to the circuit unit 50 with respect to the longitudinal axis C. In this modification, the coil axis T, which is the center of the electric receiver coil 26, extends substantially parallel to the width direction of the held unit 3.

In addition, also in this modification, the coil axis T of the electric receiver coil 26 passes through a position which is distant from the above-described magnetic members (7, 43, 50, 55), and each of the magnetic members (7, 43, 50, 55) is located distant from the coil axis T of the electric receiver coil 26. Accordingly, in this modification, too, the magnetic field, which is generated by the resonance of the electric-supplier-side resonator 21, is effectively prevented from being shielded by the magnetic members (7, 43, 50, 55) before the magnetic field is coupled to the electric receiver coil 26, and the electric power is properly supplied from the electric supplier coil 22 to the electric receiver coil 26 by the electromagnetic field resonance method (by wireless transmission).

Figure 13:
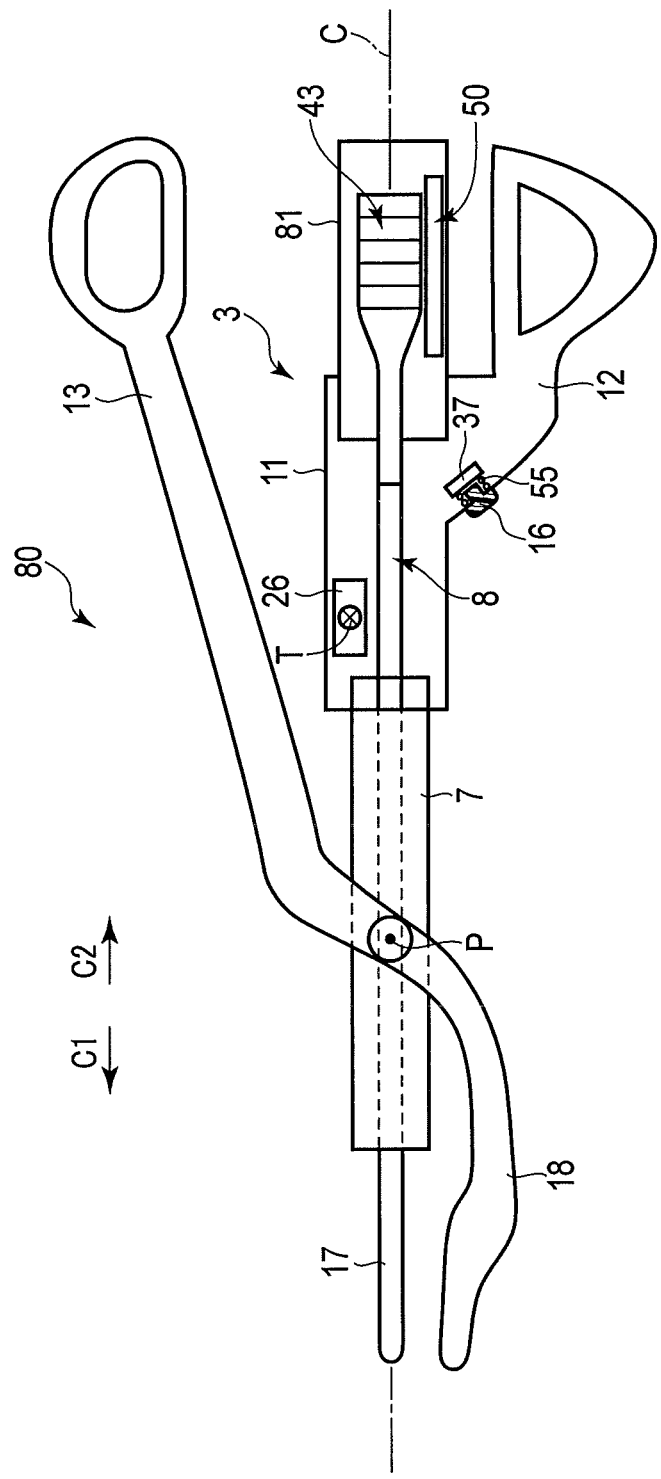
FIG. 13 is a schematic view illustrating an energy treatment instrument according to a seventh modification.

Additionally, in an energy treatment instrument (handpiece) 80 of a seventh modification illustrated in FIG. 13, the opening and closing directions of the movable handle 13 are substantially perpendicular to (cross) the longitudinal axis, and are substantially perpendicular to (cross) the width direction of the held unit (housing) 3. In this modification, the jaw 18 and movable handle 13 are rotatable as one piece. The jaw 18 and movable handle 13 are rotatable about a rotational axis P which passes through a coupling position to the sheath 7. In the present modification, the slider member 52 and elastic member 53 are not provided in the energy treatment instrument 80. Incidentally, the energy treatment instrument 80 of this modification is used for ventrotomy or the like. In addition, FIG. 13 illustrates the inside of the held unit 3 by a cross section perpendicular to the width direction of the held unit 3.

In the present modification, a transducer case 81 is coupled to the case main body 11 of the held unit 3 from the proximal side, and the ultrasonic transducer 43 is disposed in the inside of the transducer case 81. By the transducer case 81 being coupled to the case main body 11, the ultrasonic transducer 43 is coupled to the proximal portion of the vibration transmitter 8. Also in this modification, the sheath 7, vibration transmitter 8, case main body 11 and ultrasonic transducer 43 extend along the longitudinal axis C, with the centers thereof substantially agreeing with the longitudinal axis C. Furthermore, also in this modification, the ultrasonic transducer 43, sheath 7 and jaw 18 are magnetic members including a magnetic material.

In the present modification, the stationary handle 12 extends from the case body 11 in a direction crossing the longitudinal axis C. In this modification, the stationary handle 12 is located on the side opposite to the movable handle 13 with respect to the longitudinal axis C. Also in this modification, vibration generating electric power is supplied from the driving circuit 38 to the ultrasonic transducer 43, and ultrasonic vibration is generated by the ultrasonic transducer 43. In addition, the generated ultrasonic vibration is transmitted to the treatment portion 17 through the vibration transmitter 8. Furthermore, high-frequency electric power is supplied from the driving circuit 38 to the treatment portion 17 and jaw 18. In this modification, in the state in which a treated target (skin) is grasped between the treatment portion 17 and jaw 18, a ventrotomy treatment is performed by using the ultrasonic vibration and high-frequency electric power.

In the present embodiment, the circuit unit 50, which includes the converter circuit 31, controller 35 and driving circuit 38, is disposed in the inside of the transducer case 81. Like the first embodiment, the circuit unit 50 is a magnetic member including a magnetic material. In addition, in the present modification, the energy operation input button 16 is attached to the stationary handle 12, and the operation switch 37, the open state and closed state of which are changed over based on the input of the energy operation in the energy operation input button 16, is provided in the inside of the stationary handle 12. Besides, the energy operation input button 16 is urged by the urging member 55 to a position where the operation switch 37 is not pushed (i.e. a position where the operation switch 37 is set in the open state). Also in this modification, the urging member 55 is a magnetic member which is formed of a magnetic material. In this modification, the circuit unit 50, energy operation input button 16, operation switch 37 and urging member 55 are located on the side opposite to the movable handle 13 with respect to the longitudinal axis C.

In the present modification, the electric receiver coil 26 is provided in the inside of the case main body 11. The electric receiver coil 26 is located on the distal side with respect to the circuit unit 50 and urging member 55 (energy operation input button 16), and is located on the side opposite to the circuit unit 50 and urging member 55 with respect to the longitudinal axis C. In this modification, the coil axis T, which is the center of the electric receiver coil 26, extends substantially parallel to the width direction of the held unit 3.

In addition, also in this modification, the coil axis T of the electric receiver coil 26 passes through a position which is distant from the above-described magnetic members (7, 18,

43, 50, 55), and each of the magnetic members (7, 18, 43, 50, 55) is located apart from the coil axis T of the electric receiver coil 26. Accordingly, in this modification, too, the magnetic field, which is generated by the resonance of the electric-supplier-side resonator 21, is effectively prevented from being shielded by the magnetic members (7, 18, 43, 50, 55) before the magnetic field is coupled to the electric receiver coil 26, and the electric power is properly supplied from the electric supplier coil 22 to the electric receiver coil 26 by the electromagnetic field resonance method (by wireless transmission).

In the above-described embodiment, etc., the driving circuit 38 generates vibration generating electric power and high-frequency electric power as energy for use in a treatment, but the restriction to this is unnecessary. For example, in one modification, the above-described configuration may be applied to an energy treatment instrument in which a treated target is grasped between two jaws provided in a distal portion, and a heating element is provided in at least one of the jaws. In this case, by the electric power received by the electric receiver coil (26; 26A to 26C), the driving circuit 38 generates heat generating electric power (DC electric power or AC electric power) as energy for use in a treatment, and supplies the heat generating electric power to the heating element. Thereby, heat is generated by the heating element, and the heat is applied to the grasped treated target to treat the treated target.

Additionally, in another modification, the above-described configuration is applied to an energy treatment instrument which is provided with a movable portion and which treats a treated target by moving the movable portion. In this case, an electric motor, which generates a driving force for moving the movable portion, is provided, and the driving circuit 38 generates, by the electric power received by the electric receiver coil (26; 26A to 26C), driving electric power for driving the electric motor as energy for use in the treatment. For example, when the above-described configuration is applied to an energy treatment instrument having a distal portion provided with a stapler, the driving circuit 38 generates the driving electric power by the electric power received by the electric receiver coil (26; 26A to 26C), and a movable portion provided in the stapler moves by the electric motor being driven by the driving electric power. By the movable portion moving, a staple, which is accommodated in the inside of the stapler, is pushed by the movable portion, and the staple is pierced through the treated target.

Besides, the electric motor, which generates the driving force for moving the movable portion, is a magnetic member including a magnetic material. Thus, in the energy treatment instrument that is provided with the electric motor, the coil axis (T; T1 to T3) of the electric receiver coil (26; 26A to 26C) passes through a position which is distant from the electric motor.

Additionally, in the above-described embodiment, etc., the electric supplier unit 6 is disposed on the trolley as a peripheral device, but the restriction to this is unnecessary. For example, in the case of the energy treatment instrument (2) which performs a treatment by the treatment portion 17 being inserted in a body cavity, the electric supplier unit (6) may be provided in a trocar which is pierced in the body wall.

Additionally, if such a configuration is adopted that the coil axis (T; T1 to T3) of the coil (26; 26A to 26C) passes through a position which is distant from the magnetic members (7, 18, 33, 43, 50, 53, 55), the disposition of the coil (26; 26A to 26C) and the disposition of the magnetic members (7, 18, 33, 43, 50, 53, 55) in the energy treatment instrument (2; 70; 80) are not restricted to the above-described embodiment, etc., and can be modified as needed.

In the above-described embodiment, etc., the energy treatment instrument (2; 70; 80) includes the held unit (3) which has the longitudinal axis (C) and is capable of being held, and the electric-receiver-side resonator (25) including the electric receiver coil (26; 26A to 26C) which is wound around the coil axis (T; T1 to T3), the electric-receiver-side resonator being configured to resonate at the same resonance frequency (f0) as the electric-supplier-side resonator (21) including the electric supplier coil (22), thereby electric power being supplied from the electric supplier coil (22) to the electric receiver coil (26; 26A to 26C). The energy treatment instrument (2; 70; 80) includes the energy generator (38) configured to be driven by the electric power supplied from the electric supplier coil (22) to the electric receiver coil (26; 26A to 26C), and configured to generate energy for use in a treatment, and the magnetic member (7, 18, 33, 43, 50, 53, 55) which includes a magnetic material and is located distant from the coil axis (T; T1 to T3) of the electric receiver coil (26; 26A to 26C).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An energy treatment instrument comprising:
a held unit which has a longitudinal axis, and which is capable of being held, the held unit including:
a case main body which extends along the longitudinal axis; and
a stationary handle which extends from the case main body in an extension direction crossing the longitudinal axis;
an end effector exposed outside of the held unit, and configured to contact to a biological tissue;
a magnetic member including a magnetic material;
an electric-receiver-side resonator including an electric receiver coil which has a coil axis that is located distant from the magnetic member, and a capacitor, an inductance of the electric receiver coil and a capacitance of the capacitor being set in a state in which the electric-receiver-side resonator resonates at a same resonance frequency as an electric-supplier-side resonator including an electric supplier coil, the electric-receiver-side resonator being configured to resonate at the resonance frequency so that electric power for thermally denaturing the biological tissue contacted by the end effector is supplied from the electric supplier coil to the electric receiver coil during a treatment; and
an energy generator configured to generate energy for use in the treatment, by using the electric power supplied to the electric receiver coil,
wherein the magnetic member extends along the longitudinal axis of the held unit, and
the coil axis of the electric receiver coil does not intersect the longitudinal axis of the held unit when the held unit is viewed from each of one side and the other side of a width direction of the held unit which is perpendicular to the longitudinal axis and the extension direction of the stationary handle.

2. The energy treatment instrument of claim 1, wherein, when the held unit is viewed from each of one side and the other side of a direction along the longitudinal axis of the held unit, the coil axis of the electric receiver coil does not intersect the longitudinal axis of the held unit.

3. The energy treatment instrument of claim 1, wherein the held unit includes a movable handle which is openable and closable relative to the stationary handle, and
the magnetic member includes an elastic member which extends along the longitudinal axis in an inside of the case main body, and which is configured to contract by closing the movable handle relative to the stationary handle, the elastic member being located distant from the coil axis of the electric receiver coil.

4. The energy treatment instrument of claim 1, wherein the magnetic member includes an accumulator which is configured to accumulate the electric power supplied from the electric supplier coil to the electric receiver coil, the accumulator being located distant from the coil axis of the electric receiver coil.

5. The energy treatment instrument of claim 1, further comprising a vibration transmitter which extends along the longitudinal axis, and which is configured to transmit ultrasonic vibration for use in the treatment from a proximal side toward a distal side, and
the magnetic member includes a vibration generator which is coupled to a proximal portion of the vibration transmitter, and which is configured to generate the ultrasonic vibration, which is transmitted to the vibration transmitter, by being supplied with the energy from the energy generator, the vibration generator being located distant from the coil axis of the electric receiver coil.

6. The energy treatment instrument of claim 1, wherein the electric-receiver-side resonator includes at least one additional electric receiver coil,
each of the additional electric receiver coils is wound around an additional coil axis which corresponds thereto, and
the magnetic member is located distant from each of the additional coil axes.

7. The energy treatment instrument of claim 6, wherein an extending direction of the coil axis is different from an extending direction of at least one of the additional coil axes.

8. The energy treatment instrument of claim 1, wherein the electric receiver coil is disposed in the stationary handle.

9. The energy treatment instrument of claim 1, further comprising:
an operation switch provided in the held unit;
a battery which is capable of being charged with the electric power; and
a change-over switch that is capable of being changed over between a first state in which the battery and the electric-receiver-side resonator are electrically connected, and a second state in which the battery and the energy generator are electrically connected,
wherein the change-over switch is changed over from the first state to the second state, when the operation switch is activated.

10. The energy treatment instrument of claim 1, wherein the electric power is supplied from the electric supplier coil to the electric receiver coil by an electromagnetic field resonance method when a distance from electric-receiver-side resonator to the electric-supplier-side resonator is several meters or less.

11. The energy treatment instrument of claim 1, wherein the electric power is supplied from the electric supplier coil to the electric receiver coil by an electromagnetic field resonance method in a state that the held unit, the magnetic member, the electric-receiver-side resonator, and the energy generator are at least one meter apart from the electric-supplier-side resonator.

12. The energy treatment instrument of claim 1, further comprising a battery configured to electrically connect to the capacitor through a converter circuit.

13. The energy treatment instrument of claim 12, further comprising the converter circuit configured to electrically connect between the capacitor and the battery.

14. The energy treatment instrument of claim 1, wherein the energy generator generates energy for use in the denaturing simultaneously with the electric power being supplied from the electric supplier coil to the electric receiver coil during the treatment.

15. The energy treatment instrument of claim 1, wherein the coil axis of the electric receiver coil does not pass through an outer shape of the magnetic member and an inside of the outer shape of the magnetic member when the held unit is viewed from each of one side and the other side of a width direction of the held unit.

16. The energy treatment instrument of claim 2, wherein the coil axis of the electric receiver coil does not pass through an outer shape of the magnetic member and an inside of the outer shape of the magnetic member when the held unit is viewed from each of one side and the other side of a direction along the longitudinal axis of the held unit.

17. An energy treatment instrument comprising:
a held unit which has a longitudinal axis, and which is capable of being held, the held unit including:
a case main body which extends along the longitudinal axis; and
a stationary handle which extends from the case main body in an extension direction crossing the longitudinal axis;
an end effector exposed outside of the held unit, and configured to contact to a biological tissue;
a magnetic member including a magnetic material;
an electric-receiver-side resonator including an electric receiver coil which has a coil axis that is located distant from the magnetic member, and a capacitor, an inductance of the electric receiver coil and a capacitance of the capacitor being set in a state in which the electric-receiver-side resonator resonates at a same resonance frequency as an electric-supplier-side resonator including an electric supplier coil, the electric-receiver-side resonator being configured to resonate at the resonance frequency so that electric power for thermally denaturing the biological tissue contacted by the end effector is supplied from the electric supplier coil to the electric receiver coil during a treatment; and
an energy generator configured to generate energy for use in the treatment, by using the electric power supplied to the electric receiver coil,
wherein the magnetic member extends along the longitudinal axis of the held unit, and
the coil axis of the electric receiver coil does not intersect the longitudinal axis of the held unit when the held unit is viewed from each of one side and the other side of a width direction along the longitudinal axis of the held unit which is perpendicular to the longitudinal axis and the extension direction of the stationary handle.

* * * * *